United States Patent [19]

Nieminen et al.

[11] Patent Number: 5,175,376
[45] Date of Patent: Dec. 29, 1992

[54] PROCESS FOR THE PURIFICATION OF 2,6-DIISOPROPYL PHENOL

[75] Inventors: Kauko Nieminen, Masku; Peter Essen, Kaarina, both of Finland

[73] Assignee: Leiras Oy, Turku, Finland

[21] Appl. No.: 876,873

[22] Filed: Apr. 30, 1992

[30] Foreign Application Priority Data

Apr. 30, 1991 [FI] Finland .................................. 912102

[51] Int. Cl.$^5$ ...................... C07C 39/06; C07C 37/84
[52] U.S. Cl. .................... 568/781; 568/749; 568/756
[58] Field of Search ........................ 568/781, 756, 749

[56] References Cited

U.S. PATENT DOCUMENTS 2,536,040  1/1951  Davidson ............................ 568/756
4,391,998  7/1983  Wu ...................................... 568/781
4,433,181  2/1984  Holter ................................. 568/756

FOREIGN PATENT DOCUMENTS 1145628   3/1963  Fed. Rep. of Germany ...... 568/756
1768730   4/1972  Fed. Rep. of Germany .
20123733  1/1987  Japan ................................... 568/781

Primary Examiner—Werren B. Lone
Attorney, Agent, or Firm—Wolf, Greenfield & Sacks

[57] ABSTRACT

The object of the invention is a new method for the purification of 2,6-diisopropyl phenol (propofol). The invention is characterized in that the raw product obtained from the alkylation of propene with phenol is crystallized at a temperature where propofol crystallizes but the isomers and other phenol derivatives formed in the reaction are still in liquid form, i.e. at a temperature of $-25°$ to $+18°$ C. especially at $-20°$ to $-10°$ C., without a solvent or using a suitable solvent, such as hexane or petrol ether.

7 Claims, No Drawings

PROCESS FOR THE PURIFICATION OF 2,6-DIISOPROPYL PHENOL

BACKGROUND OF THE INVENTION

The object of the present invention is a process for the purification of 2,6-diisopropyl phenol.

2,6-diisopropyl phenol, i.e. propofol, is a pharmaceutically important compound which is used in anesthesia. The agent is especially well suited for use in surgical procedures of short duration because of its short halflife. The purity requirements of the agent for intravascular administration are very high, and the aim is a purity which is at least 99.9%.

Propofol is commercially available product. It is made from phenol and propene by Friedel-Crafts-alkylation, whereby in the reaction, besides the desired propofol I

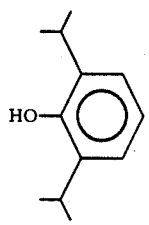

small amounts of other isomers and phenol derivatives are formed, the major contaminants being (II) 2,4- and (III) 2,5-diisopropyl phenol, (IV) 2,4,6-triisopropyl phenol, and (V) 1-isopropoxy-2,4-diisopropylbenzene.

The compounds formed in the reaction have previously been separated by fractional distillation, but this is very difficult due to the small differences in the boiling points of the compounds to be separated. Thus, after fractional distillation the product still contains up to 0.5% by weight, but normally not less than 0.3% by weight of the said contaminants, as determined mass spectrometrically. Of the above mentioned impurities, the compound 2,4-diisopropyl phenol (II) constitutes the major part, such as up to ¾, e.g. from about ¼ to about ¾ of the total contaminants.

SUMMARY OF THE INVENTION

According to the invention a process of purification has now been developed, which is based on the differences in the physical properties of the above mentioned reaction products, especially on the different solubility and crystallization characteristics of the reaction products in a specific temperature range.

Thus the process according to the invention is characterized in that the 2,6-diisopropyl phenol containing raw product obtained from the alkylation reaction of propene and phenol is purified by crystallizing the same at a temperature, which is from about $-25°$ C. up to below approximately $+18°$ C.

DETAILED DESCRIPTION

The process according to the invention is based on the surprising observation that a very high degree of purity can be achieved by crystallizing the raw product, which advantageously is a product wherein the content of contaminants has been reduced e.g. by fractional distillation as described above, at a temperature, at which propofol crystallizes but the contaminants still remain liquid. This temperature range is below approximately $+18°$ C. In this temperature range propofol crystallizes, whereas the contaminants, the boiling points of which differ only slightly from that of propofol, crystallize at substantially lower temperatures. A usable temperature is down to approximately $-25°$ C.

According to an advantageous mode, propofol is crystallized at a temperature of $-20°$ – $-10°$ C.

The crystallization can be carried out either as such, without solvent, whereby the crystallization takes place by cooling, suitably to a temperature of $-20°$ to $-10°$ C., for optimum yields. At a temperature of above $-10°$ C. the yield is not optimal although the quality of the product remains the same. The same applies to the use of temperatures below $-20°$ C. The crystallized product is then filtered and washed, preferably with a non-polar aliphatic hydrocarbon, such as, for example, hexane or petrol ether. The solvent residues contained in the product can be removed by distilling and the product itself is recovered by distillation as a very pure single fraction.

According to an alternative mode the raw product can be dissolved in an approximately 0.2 to 0.5-fold amount of a non-polar aliphatic solvent, such as hexane or petrol ether. The propofol is allowed to crystallize at a suitable temperature, it is filtered and washed as described above. The solvent residues remaining in the product are removed by evaporation. If necessary, the crystallization is repeated. The further treatment of the propofol takes advantageously place as has been described above in connection with the crystallization carried out without solvent.

The present invention allows for the preparation of a product of extremely high purity, thus allowing its safe intravascular use.

The following examples illustrate the invention without limiting the same in any way.

EXAMPLE 1

100 g of raw propofol (commercial alkylation reaction product, purity 99.7%, major contaminant compound (II) 0.2%) are placed in a flask and cooled to $-20°$ C. while vigorously stirring. After the crystallization has started, the vessel is kept at the said temperature for one hour. The crystals formed are filtered and washed with cold petrol ether. The solvent is removed by distillation from the product, whereafter the remainder is recovered by distilling as one fraction. The yield is 60 g of product with a purity of $>99.9\%$ as determined gas chromatographically.

EXAMPLE 2

100 g of raw propofol (the same as in the Example 1) and 30 g of petrol ether are placed in a flask and cooled to $-20°$ C. while stirring. After the crystallization has started, the flask is kept at the said temperature for one hour. The crystals formed are filtered and washed with cold petrol ether. The product is treated further as in Example 1, yield 60 g of product, purity $>99.9\%$.

We claim:

1. A process for the purification of 2,6-diisopropyl phenol, wherein a raw material obtained from an alkylation reaction of propene and phenol, is purified by crystallizing at a temperature range of about $-25°$ to $+18°$ C.

2. Process according to claim 1, wherein the crystallization is carried out at a temperature of $-20°$ to $-10°$ C.

3. Process according to claim 1 or 2, wherein the crystallization is carried out without a solvent.

4. Process according to claim 1 or 2, wherein the crystallization is carried out using a non-polar solvent.

5. Process according to claim 1 or 2, wherein, after crystallization, the resulting product is separated by filtration and is distilled as one fraction.

6. Process according to claim 1 or 2, wherein the raw material contains not more than 0.5% by weight of contaminants.

7. Process according to claim 4, wherein the solvent is selected from the group consisting of hexane and petrol ether.

* * * * *